(12) United States Patent
Shah et al.

(10) Patent No.: US 8,956,390 B2
(45) Date of Patent: Feb. 17, 2015

(54) DEVICES AND METHODS FOR APPLYING BOLSTER MATERIALS TO SURGICAL FASTENING APPARATUSES

(75) Inventors: Bhavin Shah, West Lafayette, IN (US); Joseph W. Zubik, Burleson, TX (US)

(73) Assignee: Cook Biotech Incorporated, West Lafayette, IN (US)

( * ) Notice: Subject to any disclaimer, the term of this patent is extended or adjusted under 35 U.S.C. 154(b) by 1099 days.

(21) Appl. No.: 12/949,857

(22) Filed: Nov. 19, 2010

(65) Prior Publication Data

US 2011/0087279 A1    Apr. 14, 2011

Related U.S. Application Data

(63) Continuation of application No. PCT/US2009/044816, filed on May 21, 2009.

(60) Provisional application No. 61/055,007, filed on May 21, 2008.

(51) Int. Cl.
*A61B 17/08*    (2006.01)
*A61B 17/072*    (2006.01)

(52) U.S. Cl.
CPC ..... *A61B 17/07207* (2013.01); *A61B 17/07292* (2013.01)
USPC ............................ 606/219; 606/213; 606/220

(58) Field of Classification Search
CPC .................... A61B 17/07207; A61B 17/07292
USPC .......................... 606/213, 219, 220; 227/175.1
See application file for complete search history.

(56) References Cited

U.S. PATENT DOCUMENTS

| | | | | |
|---|---|---|---|---|
| 5,902,312 A * | 5/1999 | Frater et al. | ................... | 606/148 |
| 6,206,931 B1 | 3/2001 | Cook et al. | | |
| 7,665,646 B2 * | 2/2010 | Prommersberger | ....... | 227/175.1 |
| 7,845,533 B2 * | 12/2010 | Marczyk et al. | ........... | 227/175.1 |
| 8,028,883 B2 * | 10/2011 | Stopek | ........................ | 227/175.1 |
| 2006/0004407 A1 * | 1/2006 | Hiles et al. | ..................... | 606/215 |
| 2007/0027472 A1 | 2/2007 | Hiles | | |

OTHER PUBLICATIONS

Heeschen C., et al., "Nicotine stimulates angiogenesis and promotes tumor growth and atherosclerosis," Nature Medicine 7 (2001), No. 7, 833-839.

Johnson C., et al., "Matrix Metalloproteinase-9 is Required for Adequate Angiogenic Revascularization of Ischemic Tissues: Potential Role in Capillary Branching," Circulation Research 94 (2004), No. 2, pp. 262-268.

* cited by examiner

*Primary Examiner* — Julian W Woo
*Assistant Examiner* — Lucas Paez
(74) *Attorney, Agent, or Firm* — Woodard, Emhardt, Moriarty, McNett & Henry LLP (57) ABSTRACT

The present invention provides, in certain aspects, medical systems that are useful for applying bolster material to patient tissue. One such system includes a surgical fastening apparatus that is comprised of a first arm having a first arm working surface; and a cutting element operable along a cutting path. This system also includes at least one piece of bolster material having a portion received in the cutting path, and a retaining element retaining the at least one piece of bolster material in association with the first arm working surface, wherein the retaining element has one or more segments received in the cutting path and includes portions residing between the first arm working surface and the at least one piece of bolster material. The invention also provides medical devices that are useful for applying bolster materials to surgical fastening apparatuses, as well as methods for preparing and using such devices.

21 Claims, 3 Drawing Sheets

DEVICES AND METHODS FOR APPLYING BOLSTER MATERIALS TO SURGICAL FASTENING APPARATUSES

REFERENCE TO RELATED APPLICATIONS

This application is a continuation of International Application No. PCT/US2009/044816, filed May 21, 2009, which claims the benefit of U.S. Provisional Application No. 61/055,007, filed May 21, 2008, each of which is hereby incorporated by reference.

BACKGROUND

The present invention relates generally to medical devices and in particular aspects to devices and methods that are useful for applying bolster materials to devices for inserting surgical fasteners, e.g., surgical staplers.

As further background, surgical stapler devices are designed to seal or simultaneously cut and seal an extended segment of tissue in a patient. Some surgical staplers include two stapler arms, a first arm including two or more lines of multiple staples (also called a "cartridge" or "jaw") and a second arm including an anvil or other feature adapted to bend each of the staples into a closed position upon operation of the stapler. So-called "anastomotic" staplers include a surgical blade in the device to sever tissue between the lines of staples. Those without such a cutting blade have been referred to as "non-anastomotic" staplers.

For some medical procedures, the use of bare staples, with the staples in direct contact with the patient's tissue, is generally acceptable. The integrity of the patient's tissue itself will normally serve to prevent the staples from tearing out of the tissue and compromising the seam before healing has occurred. However, in other procedures, the patient's tissue to be sealed is too fragile to securely hold the staples in place. For example, in the case of lung tissue, and in particular diseased lung tissue, the tissue to be stapled is fragile and, in some cases, will easily tear through unprotected staple lines. With the growing use of surgical staplers in operations on diseased lung tissues such as bullectomies and volume reduction procedures, it has become increasingly important to take measures to protect fragile tissue from tissue tears due to surgical staples or surgical stapling procedures.

One known protective measure involves the use of a reinforcement or bolster material, wherein the staples are inserted both through the bolster material and the patient's tissue. In many cases, as a preliminary step, the reinforcement material is in some manner applied to the arms of the surgical stapler, e.g. with portions applied to each arm, and the stapler thereafter used to secure tissue of the patient.

There remain needs for improved and/or alternative devices and methods for applying bolster material to surgical fastening devices, as well as systems and methods that are useful for applying bolster material to patient tissue. The present invention is addressed to those needs.

SUMMARY

The present invention provides, in certain aspects, methods for applying bolster materials to surgical fastening apparatuses. Illustratively, one such method comprises the steps of: (a) providing a surgical fastening apparatus, wherein the surgical fastening apparatus is comprised of: (i) a first arm having a first arm working surface; and (ii) a cutting element operable along a cutting path; b) providing a medical device, wherein the medical device is comprised of: (i) at least one piece of bolster material configured for application to the first arm working surface, wherein the at least one piece of bolster material has a severable bolster portion to be received in the cutting path; (ii) a retaining element associated with the at least one piece of bolster material and providing a receiving area, wherein the retaining element is adapted to hold the at least one piece of bolster material in association with the first arm working surface and includes a severable retaining element portion to be received in the cutting path; and (iii) a removable support element extending at least partially along the at least one piece of bolster material and received through the receiving area, wherein the removable support element is longitudinally slidable within the receiving area for removal from the receiving area; c) removing the removable support member from the receiving area; and d) positioning at least a portion of the surgical fastening apparatus first arm within the receiving area, wherein the at least one piece of bolster material is held in association with the first arm working surface, and the severable bolster portion and the severable retaining element portion are received in the cutting path. In some aspects, this bolster material comprises a remodelable, angiogenic ECM material, for example, a submucosa material such as small intestinal submucosa (SIS). Suitable surgical fastening apparatuses can include but are not limited to surgical staplers.

In another embodiment, the invention provides a medical device that is useful for applying a bolster material to a surgical fastening apparatus such as that described above. This medical device is comprised of: (a) at least one piece of bolster material configured for application to the first arm working surface; (b) a retaining element associated with the at least one piece of bolster material to provide a receiving area, wherein the retaining element is adapted to hold the at least one piece of bolster material in association with the first arm working surface and includes a severable retaining element portion to be received in the cutting path; and (c) a removable support element extending at least partially along the at least one piece of bolster material and received through the receiving area, wherein the removable support element is longitudinally slidable within the receiving area for removal from the receiving area.

Another aspect of the present invention provides a medical system that is useful for applying bolster material to patient tissue. This medical system is comprised of: (a) a surgical fastening apparatus which includes a first arm having a first arm working surface; and a cutting element operable along a cutting path; (b) at least one piece of bolster material having a portion received in the cutting path; and (c) a retaining element retaining the at least one piece of bolster material in association with the first arm working surface, wherein the retaining element has one or more segments received in the cutting path and includes portions residing between the first arm working surface and the at least one piece of bolster material. In some forms, this retaining element comprises at least one piece of suture material.

A further embodiment of the present invention provides a medical device that is useful for applying a bolster material to a surgical fastening apparatus, wherein the apparatus comprises a first arm having a first arm working surface; and a cutting element operable along a cutting path. This medical device comprises: (a) at least one piece of bolster material configured for application to the first arm working surface, wherein the at least one piece of bolster material has a first bolster segment positioned to occur on a first side of the cutting path and a second bolster segment positioned to occur on a second side of the cutting path; and (b) a retaining element adapted to hold the at least one piece of bolster material in association with the first arm working surface, wherein the retaining element passes through the at least one piece of bolster material in at least one location in the first bolster segment and in at least one location in the second bolster segment, and presents one or more severable retaining element segments positioned to occur in the cutting path upon application of the at least one piece of bolster material to the first arm working surface.

Other objects, embodiments, forms, features, advantages, aspects, and benefits of the present invention shall become apparent from the detailed description and drawings included herein.

DETAILED DESCRIPTION

While the present invention may be embodied in many different forms, for the purpose of promoting an understanding of the principles of the present invention, reference will now be made to the embodiments illustrated in the drawings, and specific language will be used to describe the same. It will nevertheless be understood that no limitation of the scope of the invention is thereby intended. Any alterations and further modifications in the described embodiments and any further applications of the principles of the present invention as described herein are contemplated as would normally occur to one skilled in the art to which the invention relates.

As disclosed above, in certain aspects, the present invention provides medical devices that are useful for applying bolster material to surgical fastening apparatuses, as well as methods for preparing and using such devices. Illustratively, one such device is useful for applying a bolster material to a surgical fastening apparatus having: (i) a first arm having a first arm working surface; and (ii) a cutting element operable along a cutting path. This device is comprised of: (a) at least one piece of bolster material configured for application to the first arm working surface; (b) a retaining element associated with the at least one piece of bolster material to provide a receiving area, wherein the retaining element is adapted to hold the at least one piece of bolster material in association with the first arm working surface and includes a severable retaining element portion to be received in the cutting path; and (c) a removable support element extending at least partially along the at least one piece of bolster material and received through the receiving area, wherein the removable support element is longitudinally slidable within the receiving area for removal from the receiving area. The invention also provides medical systems and related methods that are useful for applying bolster material to patient tissue, as well as medical products that include inventive devices and systems enclosed within sterile packaging.

While embodiments of the present invention are at times described herein in connection with (and in some forms, including) a surgical stapling device, it will be understood that these embodiments represent only a fraction of those of the invention. Devices of the invention may be used in conjunction with a variety of surgical fastening devices that insert fasteners of various designs including, for example, one-part and multiple (e.g., two) part staples, tacks, or other penetrating fasteners where bolstering may provide a benefit.

In some embodiments, the present invention involves the use of anastomotic staplers having a first arm and a second arm presenting respective first and second opposed working surfaces, wherein one of the arms (i.e., the "cartridge" or "jaw") holds two or more rows of implantable staples, and a second arm ("anvil") contains corresponding means to bend each of the staples into a "closed" position during a stapling procedure. The size, shape, and configuration of each of these arms, as well as the dimensions of their working surfaces, can vary. Such apparatuses include a cutting element that is operable along a cutting path. This path runs along and between passages (e.g., slots, apertures, etc.) in the cartridge side working surface through which the two or more rows of staples can pass during a stapling procedure. This cutting element can be any suitable object or device that is useful for severing objects positioned in the cutting path during operation of the stapler, for example, severable portions of a bolster material, patient tissue, and severable portions of a retaining element such as a retaining suture. Although not necessary to broader aspects of the present invention, a suitable cutting element can be a cutting blade or other similar implement.

Figure 1:
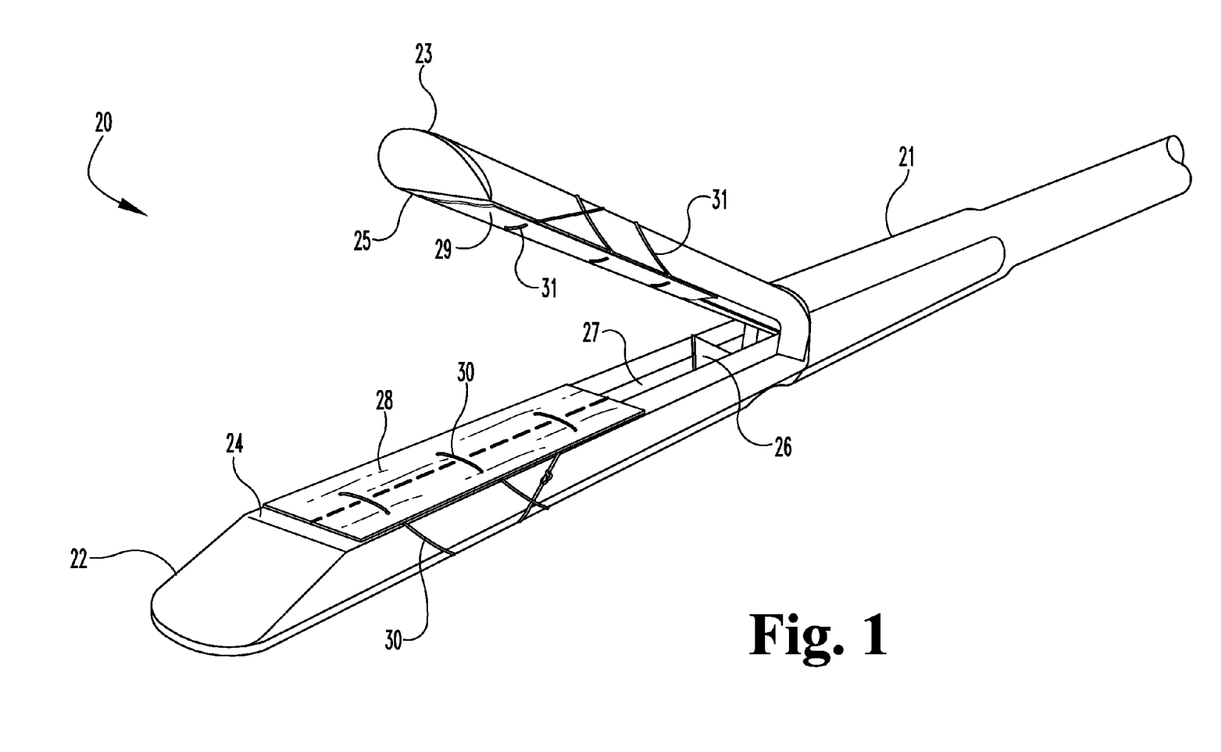
FIG. 1 is a perspective view of a medical system of the present invention.

With reference now to FIG. 1, shown is a perspective view of a medical system 20 of the present invention that is useful for applying bolster material to patient tissue. Medical system 20 includes a surgical stapler 21 having a first arm 22 and a second arm 23, which provide a first arm working surface 24 and a second arm working surface 25, respectively. Surgical stapler 21 further includes cutting blade 26, which can be moved along cutting path 27. Medical system 20 further includes a first piece of bolster material 28 and a second piece of bolster material 29, which are applied to first arm working surface 24 and second arm working surface 25, respectively. Additionally, medical system 20 includes a first retaining suture 30 retaining first piece of bolster material 28 in association with first arm working surface 24 and a second retaining suture 31 retaining second piece of bolster material 29 in association with second arm working surface 25. As shown in FIG. 1, first piece of bolster material 28 and first retaining suture 30 have portions received in cutting path 27 and positioned to be severed by cutting blade 26 during a stapling procedure. In this depiction, surgical stapler 21 is shown in an open condition. When stapler 21 is placed in a generally closed condition, second arm 23 approaches first arm 22, locating portions of second piece of bolster material 29 and portions of second retaining suture 31 in positions to be severed by cutting blade 26.

Figure 2:
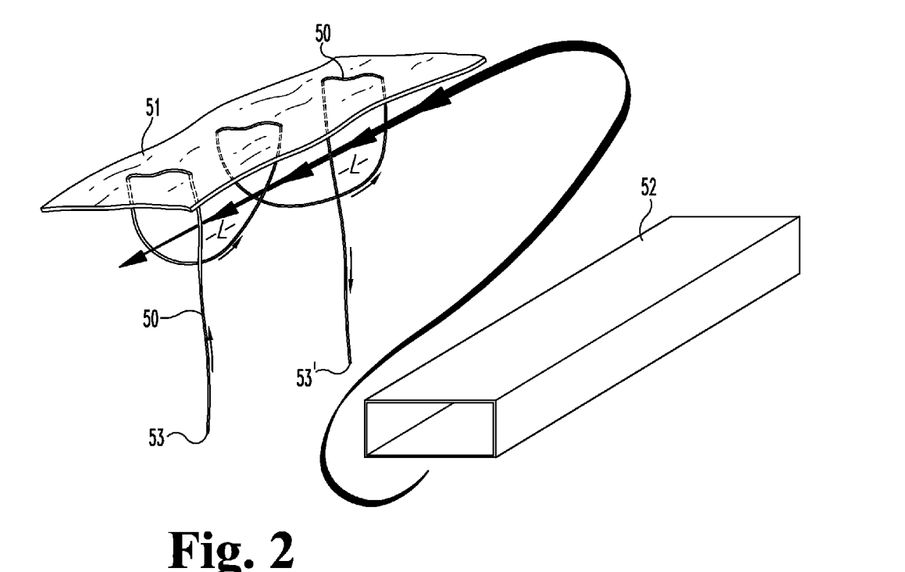
FIG. 2 shows a step in a method of the invention for a forming a medical device that is useful for applying a bolster material to a surgical fastening apparatus.
Figure 3:
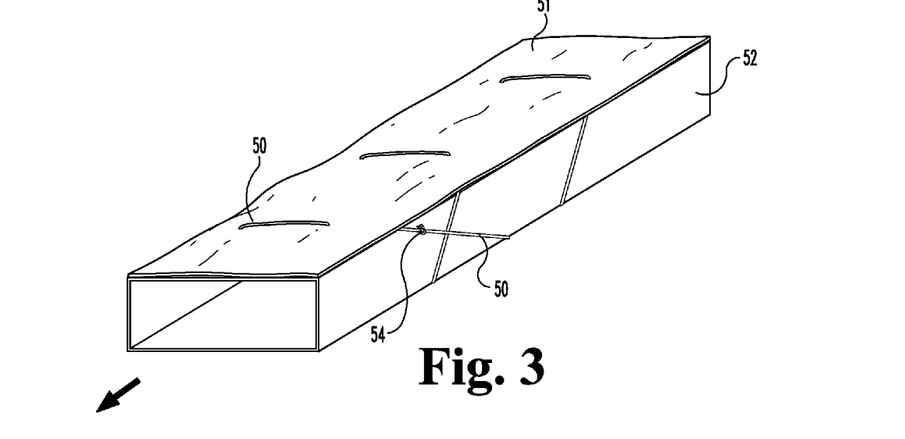
FIG. 3 is a perspective view of an assembled medical device of the invention.

FIGS. 2 and 3 show steps in a method of the invention for assembling a medical device that is useful for applying a bolster material to a surgical fastening apparatus, e.g., to an arm of a surgical stapler such as the stapler depicted in FIG. 1. As shown in FIG. 2, a continuous suture strand 50 can be threaded in the direction of the smaller arrows through a piece of bolster material 51 to provide a space (e.g., a passageway) through which a removable support element 52 can be received (as shown by the larger arrows). This space or receiving area is generally defined by one side of bolster material piece 51 and looped portions L of suture strand 50 extending from this bolster material side. When formed in this fashion, the receiving area can at first be made large enough for the support element 52 to easily pass therethrough. Then, upon suitably positioning support element 52 in the receiving area, the ends of suture strand 50 can be pulled tight and secured together so that support element 52 becomes snugly fit within the receiving area (yet is longitudinally slidable therein to allow for subsequent removal). Suture stand 50 can exhibit any suitable size, shape and configuration, and may be formed with one or more of a variety of suitable materials.

While this particular retaining element-bolster material combination and configuration is certainly useful, it represents only one embodiment of the present invention. As described more thoroughly below, other suitable component combinations and configurations are contemplated for holding one or more pieces of bolster material in association with a working surface of a surgical fastening apparatus in accordance with the present invention. In this regard, it will be understood that retaining elements useful in the invention can be formed with something other than suture material, and receiving areas need not be defined by one or more looped elements. Nonetheless, it should be noted that when suture material is used as all or part of a retaining element in the invention, it may be provided as one or more individual suture pieces, any one of which may or may not be associated with a bolster material piece in the fashion shown in FIGS. 2 and 3 (i.e., a suture strand need not pass through a bolster material piece the same number of times or in the same locations on the material as shown).

Further in this regard, retaining elements useful in some forms of the invention are comprised of one or more non-suture objects or devices, for example, single- or multiple part adaptations such as but not limited to straps, hooks or hook-like devices, fasteners, and other similar objects which are capable of holding or at least helping to hold a piece of bolster material in association with a fastening apparatus working surface in accordance with the present invention, while including a severable retaining element portion to be received in a fastening apparatus cutting path. Such non-suture objects and devices can exhibit any suitable size, shape, and configuration, and may be formed with one or more of a variety of materials, any of which may be rigid, malleable, semi-flexible, or flexible.

Continuing with FIGS. 2 and 3, removable support element 52 can be received through the receiving area as indicated by the larger arrows in FIG. 2. (Although not shown here, the removable support element can have a tapered end portion or other similar feature(s) to facilitate its passage into and through the receiving area.) Thereafter, opposing suture end portions 53 and 53' can be brought together (around support 52) and secured to form knot 54. This will provide an arrangement as illustrated, in which removable support element 52 can be removed and discarded either before or during a loading procedure, i.e., a procedure involving the application of bolster material piece 51 to an arm of a surgical fastening device.

Forming knot 54 provides a generally fixed receiving area around support element 52 as shown in FIG. 3. However, in this context, it will be understood that use of the term "generally fixed" does not necessarily mean that the dimensions of the receiving area cannot change once the suture end portions 53 and 53' are fixed together. In some embodiments, the suture strand has very little or no elasticity, so that the dimensions of the receiving area will not change (or change very little) once the suture ends are tightly secured in place around a support element. In other embodiments, the suture strand exhibits a degree of elasticity, so that the general volume of the receiving area can change once the suture ends are tightly secured to one another. In the latter embodiments, a fixed, yet expandable receiving area can be caused to expand to facilitate removal of a support element therefrom. Then, with a surgical fastener arm positioned in the expanded receiving area, the receiving area can be allowed to contract to provide a snug fit around the arm.

Regardless of whether suture strand 50 has an elasticity, it will be understood that in pulling tight and securing suture end portions 53 and 53', varying degrees of snugness can be provided in the fit between the support element 52 and the bolster material-suture strand combination. In general, a suitable fit is one that at least allows (i) the support element 52 to be removed (e.g., slid) from the receiving area without undesirably affecting the bolster material-suture strand combination; and (ii) the bolster material to be desirably held in association with a surgical fastening apparatus arm working surface upon application of the bolster material-suture strand combination to the fastening apparatus.

While certainly useful, the above-described order in which the suture strand 50, bolster material piece 51, and removable support element 52 are assembled together is not limiting of the present invention. Any suitable method, as well as any suitable sequence of steps therein, may be used to form medical devices of the invention. Further, suture end portions 53 and 53' may be secured together in any suitable manner including but not limited to hooking or otherwise fastening them together, welding them together, and/or using an adhesive.

Again, a variety of surgical fastening apparatuses may be used in conjunction with the present invention, and in this regard, a removable support element, when used in the invention, can be exhibit any suitable size, shape and configuration, and can be formed with one or more of a variety of suitable materials (e.g., a metallic or synthetic polymeric material) to facilitate formation of a desirable receiving area for receiving an arm of one of these apparatuses. In some forms, differently sized and configured support elements will be required for the cartridge and anvil sides of a surgical stapler. Although removable support element 52 is generally in the form of a hollow, rectilinear tube, a support element useful in the invention, or any portion thereof, can exhibit any suitable three-dimensional rectilinear or curvilinear shape. Such three-dimensional rectilinear shapes can have any practical number of sides, and can include, for example, cubes, cuboids, tetrahedrons, prisms, pyramids, wedges, and variations thereof. Suitable three-dimensional curvilinear bodies include but are not limited to spheres, spheroids, ellipsoids, cylinders, cones, and variations thereof (e.g., a segment of a sphere, or a truncated cone, etc.).

Although not necessary to broader aspects of the invention, the dimensions of a particular support element can be configured to approximate those of the fastening apparatus arm for which the receiving area is being formed. For example, in the current embodiment, the height and width of the hollow support tube 52 generally corresponds with that of the main, working surface portion of the surgical fastening apparatus arm depicted in FIGS. 4 and 5. In this regard, bolster material piece 51, which (as shown in FIG. 3) overlaps a major lateral portion of one side of the support element 52, is sufficient (when applied to the fastening apparatus arm as shown in FIG. 5) to overlap a major lateral portion of working surface 61. As well, the length of bolster material piece 51 can be varied as desired, and will generally be sufficient to cover portions of the arm's working surface through which fasteners are able to pass.

Upon tying together suture end portions 53 and 53', any loose suture material can be trimmed away from knot 54, and removable support element 52 can be removed from the receiving area in the direction of the arrow shown in FIG. 3. In some modes of operation, a removable support element such as that shown in FIGS. 2 and 3 can be manipulated (e.g., cut, trimmed, torn, bent, etc.) to facilitate its removal from a tight-fitting receiving area. In certain embodiments, a support element is equipped with one or more features for this purpose, e.g., it may be collapsible.

Figure 4:
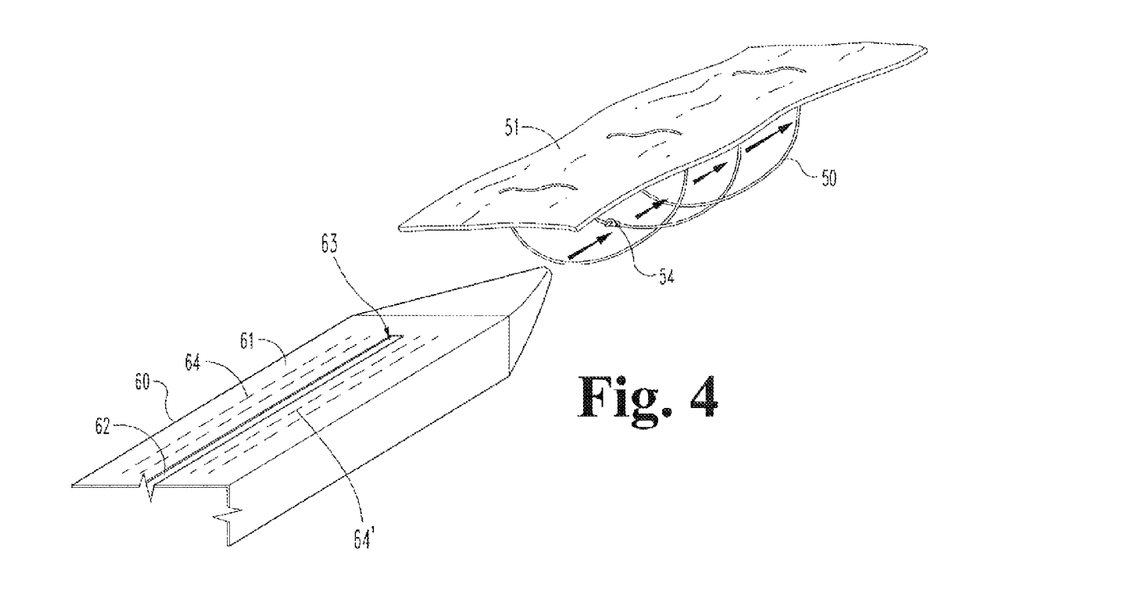
FIG. 4 shows a step in a method of the invention for forming a medical system that is useful for applying bolster material to patient tissue.
Figure 5:
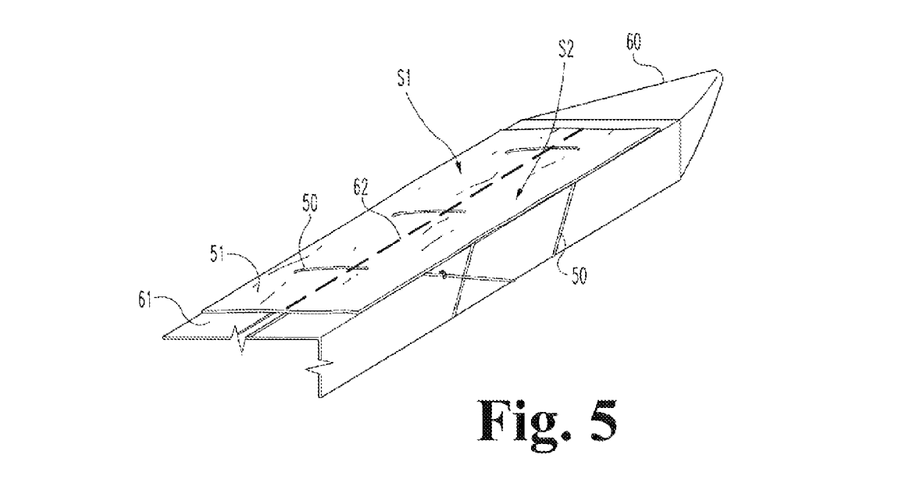
FIG. 5 is a partial, perspective view of another medical system of the invention.

After removal of support element 52 from the receiving area (and referring now to FIGS. 4 and 5 together), a surgical fastening apparatus arm 60 having a working surface 61 can be suitably aligned with and received through the receiving area in the direction of the arrows depicted in FIG. 4. In alternative embodiments, removal of support element 52 from the receiving area occurs simultaneously with positioning of the surgical fastening apparatus arm 60 within the receiving area. For example, a support element can be slid from one end of a receiving area while a surgical fastening apparatus arm is being received in the opposite end, and in some forms, the support element is configured to releasably engage with the apparatus arm to facilitate such a process. Other suitable techniques may be used to facilitate removal of a support element from (and positioning of a fastening apparatus arm within) a receiving area so as to not undesirably affect the integrity of a bolster material piece and/or retaining element. For example, the retaining element, support element, and/or bolster material may include (and/or be coated with) a substance designed to enhance the slidability between or among surfaces involved in a removal or loading step.

Arm 60 also includes a cutting path 62, which runs longitudinally along working surface 61 and separates opposing rows of staple recesses 64 and 64'. Cutting path 62 is generally defined by space in and around a slot 63 in which a cutting element such as a blade can travel. Again, the devices and systems of the present invention can be used in conjunction with a variety of surgical fastening devices, and therefore, it will be understood that their use with a variety of differently sized, shaped, and configured cutting paths and cutting elements is contemplated as well.

FIG. 5 shows bolster material piece 51 applied to working surface 61, and held in association therewith by suture strand 50, with portions of suture strand 50 residing between bolster material piece 51 and working surface 61. In this configuration, bolster material piece 51 is generally aligned with working surface 61 so that it overlaps a major lateral portion of working surface 61 and longitudinally covers opposing rows of staple recesses 64 and 64'. As shown, bolster material piece 51 includes a first bolster segment S1 and a second bolster segment S2 separated by cutting path 62. Also, bolster material piece 51 and suture strand 50 both have portions received in cutting path 62, positioned to be cut by a cutting blade or other cutting element during a surgical fastening procedure. Illustratively, in one such procedure, a surgical stapling apparatus, which includes a first arm (similar to arm 60) and a second arm, are positioned around tissue to be cut and then locked firmly together. A surgeon can then actuate the stapler device, simultaneously installing and "setting" two or more lines of staples through the tissue, and operating a cutting blade on a cutting path that severs a severable retaining element portion, patient tissue, and a severable bolster material portion. Thereafter, all portions of suture strand 50 can be removed from the treatment site.

If needed, a sticking agent can be used to facilitate temporary adhesion of a piece of bolster material to an arm working surface. Any substance that increases the attachment of the bolster material to the working surface can be used, so long as the attachment is not so permanent as to undesirably interfere with release of the bolster material from the working surface after the surgical stapler has been fired or otherwise actuated to insert the staple or staples. Such sticking agents can include inorganic, organic, natural and/or synthetic substances. In many cases, biocompatible surgical lubricants will suffice to improve this adhesion. Biocompatible adhesive materials, including pressure-sensitive adhesives, may also be used, including for example polyvinyl pyrrolidones, polyvinyl alcohols, polyvinyl acetates, vinyl acetate esters, starches, dextrins, acrylic resins, polyurethanes, styrene/butadiene radon copolymers, silicones, polyisobutylenes, polyisoprene polyvinyl ethyl ether and copolymers, blends or combinations thereof. The adhesive can be applied to the working surface and/or bolster material piece before and/or after the piece is applied to the working surface.

Turning now to a discussion of bolster materials, it will be understood that in preparing and using medical devices and systems of the present invention, one piece, or more than one piece of bolster material, can be applied to an arm of a surgical stapler or other fastening apparatus. Suitable bolster materials are generally biocompatible, and in some embodiments of the invention, are comprised of reconstituted or naturally-derived collagenous materials. Such materials that are at least bioresorbable will provide advantage in the present invention, with materials that are bioremodelable and promote cellular invasion and ingrowth providing particular advantage.

Suitable bioremodelable materials can be provided by collagenous extracellular matrix materials (ECMs) possessing biotropic properties, including in certain forms angiogenic collagenous extracellular matrix materials. For example, suitable collagenous materials include ECMs such as submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa, including small intestinal submucosa, stomach submucosa, urinary bladder submucosa, and uterine submucosa.

As prepared, the submucosa material and any other ECM used may optionally retain growth factors or other bioactive components native to the source tissue. For example, the submucosa or other ECM may include one or more growth factors such as basic fibroblast growth factor (FGF-2), transforming growth factor beta (TGF-beta), epidermal growth factor (EGF), platelet derived growth factor (PDGF), and/or cartilage derived growth factor (CDGF). As well, submucosa or other ECM used in the invention may include other biological materials such as heparin, heparin sulfate, hyaluronic acid, fibronectin and the like. Thus, generally speaking, the submucosa or other ECM material may include a bioactive component that induces, directly or indirectly, a cellular response such as a change in cell morphology, proliferation, growth, protein or gene expression.

Submucosa or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multiaxial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination.

Such non-collagenous solids can constitute a significant percentage of the dry weight of the ECM material in certain inventive embodiments, for example at least about 1%, at least about 3%, and at least about 5% by weight in various embodiments of the invention.

The submucosa or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

Further, in addition or as an alternative to the inclusion of native bioactive components, non-native bioactive components such as those synthetically produced by recombinant technology or other methods, may be incorporated into the submucosa or other ECM tissue. These non-native bioactive components may be naturally-derived or recombinantly produced proteins that correspond to those natively occurring in the ECM tissue, but perhaps of a different species (e.g. human proteins applied to collagenous ECMs from other animals, such as pigs). The non-native bioactive components may also be drug substances. Illustrative drug substances that may be incorporated into and/or onto the ECM materials used in the invention include, for example, antibiotics, thrombus-promoting substances such as blood clotting factors, e.g. thrombin, fibrinogen, and the like. These substances may be applied to the ECM material as a premanufactured step, immediately prior to the procedure (e.g. by soaking the material in a solution containing a suitable antibiotic such as cefazolin), or during or after engraftment of the material in the patient.

Submucosa or other ECM tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of the submucosa tissue used in the present invention.

When used in the invention, a typical layer thickness for an as-isolated submucosa or other ECM tissue layer ranges from about 50 to about 250 microns when fully hydrated, more typically from about 50 to about 200 microns when fully hydrated, although isolated layers having other thicknesses may also be obtained and used. These layer thicknesses may vary with the type and age of the animal used as the tissue source. As well, these layer thicknesses may vary with the source of the tissue within the animal source. When a piece of submucosa or other ECM material having differing characteristic sides is used in the invention, it can be applied to a surgical fastening apparatus arm with a specified side contacting the working surface of the arm. For example, in the case of small intestinal submucosa, the material may be oriented with either the luminal or abluminal side contacting the arm's working surface.

Bolster materials useful in some forms of the invention can include xenograft components (i.e., cross species material, such as tissue material from a non-human donor to a human recipient), allograft components (i.e., interspecies material, with tissue material from a donor of the same species as the recipient), and/or autograft components (i.e., where the donor and the recipient are the same individual). For example, in certain aspects of the invention, a bolster material includes ECM tissue material, wherein the ECM material is xenogenic relative to the patient receiving the bolster implant, and any added exogenous substances are from the same species (e.g. autologous or allogenic) as the patient receiving the implant. Illustratively, human patients may be treated with xenogenic ECM bolster material (e.g. porcine-, bovine- or ovine-derived material) that has been combined with exogenous human material(s) as described herein, those exogenous materials being naturally derived and/or recombinantly produced.

Other implantable materials may be employed as bolster materials in the present invention including non-bioresorbable and bioresorbable synthetic polymer materials such as polytetrofluroethylene (PTFE, e.g. GORE-TEX material), nylon, polypropylene, polyurethane, silicone, DACRON polymer, polyglycolic acid (PGA), polylactic acid (PLA), polycaprolactone, and others.

In certain embodiments of the invention, the bolster material will have a thickness in the range of about 50 to about 1000 microns, more preferably about 100 to 600 microns, and most preferably about 100 to about 350 microns. The bolster material will desirably provide sufficient strength to effectively reinforce any staples or other fasteners used, for example, exhibiting a suture retention strength in the range of about 100 to about 1000 gram force, e.g., typically in the range of about 200 to about 600 gram force, each of these based upon 5-0 Prolene suture and a bite depth of 2 mm. If necessary or desired, a multilaminate bolster material can be used. For example, a plurality of (i.e., two or more) layers of collagenous material, for example, submucosa-containing or other ECM material, can be bonded together to form a multilaminate structure useful as a bolster material. Illustratively, two, three, four, five, six, seven, or eight or more collagenous layers containing submucosal or other collagenous ECM materials can be bonded together to provide a multilaminate collagenous bolster material. In certain embodiments, two to six collagenous, submucosa-containing layers isolated from intestinal tissue of a warm-blooded vertebrate (e.g., small intestinal tissue), are bonded together to provide the bolster material. Porcine-derived small intestinal tissue may be used for this purpose. The layers of collagenous tissue can be bonded together in any suitable fashion, including dehydrothermal bonding under heated, non-heated or lyophilization conditions, using adhesives, glues or other bonding agents, crosslinking with chemical agents or radiation (including UV radiation), or any combination of these with each other or with other suitable methods.

The medical devices and systems of the present invention are useful in a variety of surgical procedures. Such procedures include but are not limited to various lung resection procedures (e.g., blebectomies, lobectomoies, bullectomies, wedge resections, and lung reduction procedures, such as those used to treat symptoms of emphysema); treatment of soft tissue injuries and defects (e.g., abdominal or thoracic wall procedures, gastro-intestinal procedures), and a variety of other surgical procedures (e.g., reproductive organ repair procedures, etc.). In this regard, the medical devices and systems of the invention may be used in conjunction with operations on both humans and animals.

The medical devices and systems of the invention can be provided in sterile packaging suitable for medical products. Sterilization may be achieved, for example, by irradiation, ethylene oxide gas, or any other suitable sterilization technique, and the materials and other properties of the medical packaging will be selected accordingly.

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. A method for applying a bolster material to a surgical fastening apparatus prior to operating the apparatus to insert one or more surgical fasteners through at least one piece of bolster material, the method comprising:
   a) providing a surgical fastening apparatus, the surgical fastening apparatus comprising:
      a first arm having a first arm working surface; and
      a cutting element operable along a cutting path;
   b) providing a medical device, the medical device comprising:
      the at least one piece of bolster material configured for application to the first arm working surface, the at least one piece of bolster material having a severable bolster portion to be received in the cutting path;
      a retaining element associated with the at least one piece of bolster material and providing a receiving area, the retaining element adapted to hold the at least one piece of bolster material in association with the first arm working surface and including a severable retaining element portion to be received in the cutting path; and
      a removable support element extending at least partially along the at least one piece of bolster material and received through the receiving area, wherein the removable support element is longitudinally slidable within the receiving area for removal from the receiving area;
   c) prior to operating the apparatus to insert the surgical fasteners through the at least one piece of bolster material, removing the removable support element from the receiving area; and
   d) prior to operating the apparatus to insert the surgical fasteners through the at least one piece of bolster material, positioning at least a portion of the surgical fastening apparatus first arm within the receiving area, wherein the at least one piece of bolster material is held in association with the first arm working surface, and the severable bolster portion and the severable retaining element portion are received in the cutting path.

2. The method of claim 1, wherein the at least one piece of bolster material comprises collagen.

3. The method of claim 2, wherein the at least one piece of bolster material comprises an extracellular matrix material.

4. The method of claim 3, wherein the extracellular matrix material comprises serosa, pericardium, dura mater, peritoneum, or dermal collagen.

5. The method of claim 3, wherein the extracellular matrix material comprises submucosa.

6. The method of claim 5, wherein the submucosa is small intestinal submucosa.

7. The method of claim 1, wherein the cutting element is a cutting blade.

8. The method of claim 1, wherein the retaining element comprises suture material.

9. A medical device useful for applying a bolster material to a surgical fastening apparatus, the apparatus comprising (a) a first arm having a first arm working surface; and (b) a cutting element operable along a cutting path, the medical device comprising:
   at least one piece of bolster material configured for application to the first arm working surface;
   a retaining element associated with the at least one piece of bolster material to provide a receiving area, the retaining element including a severable retaining element portion to be received in the cutting path, and the retaining element adapted to hold the at least one piece of bolster material in association with the first arm working surface when the severable retaining element portion is in an unsevered condition; and
   a removable support element extending at least partially along the at least one piece of bolster material and received through the receiving area, wherein the removable support element is longitudinally slidable within the receiving area for removal from the receiving area and removable from the bolster material when the severable retaining element portion is in the unsevered condition.

10. The medical device of claim 9, wherein the at least one piece of bolster material comprises a collagenous material.

11. The medical device of claim 9, wherein the at least one piece of bolster material comprises a remodelable material.

12. The medical device of claim 11, wherein the remodelable material comprises collagen.

13. The medical device of claim 12, wherein the at least one piece of bolster material comprises a remodelable angiogenic extracellular matrix material.

14. The medical device of claim 13, wherein the remodelable angiogenic extracellular matrix material comprises small intestine submucosa, urinary bladder submucosa, or stomach submucosa.

15. The medical device of claim 9, wherein the retaining element comprises a suture material.

16. The medical device of claim 15, wherein the retaining element is a continuous suture strand, the suture strand being received through the at least one piece of bolster material in two or more locations and joined to itself to provide the receiving area.

17. A medical system useful for applying bolster material to patient tissue, comprising:
   a surgical fastening apparatus comprising (i) a first arm having a first arm working surface; and (ii) a cutting element operable along a cutting path;

at least one piece of bolster material having a portion received in the cutting path; and a retaining element retaining the at least one piece of bolster material in association with the first arm working surface, the retaining element having one or more segments received in the cutting path and including portions residing between the first arm working surface and the at least one piece of bolster material;

wherein the retaining element presents a plurality of loops longitudinally spaced from one another along a length of the at least one piece of bolster material and defining a receiving area arranged to receive the first arm of the surgical fastening apparatus.

18. The medical system of claim 17, wherein the at least one piece of bolster material comprises a remodelable angiogenic extracellular matrix material.

19. The medical system of claim 18, wherein the remodelable angiogenic extracellular matrix material comprises porcine small intestinal submucosa.

20. A medical device useful for applying a bolster material to a surgical fastening apparatus, the apparatus comprising (a) a first arm having a first arm working surface; and (b) a cutting element operable along a cutting path, the medical device comprising:

at least one piece of bolster material configured for application to the first arm working surface, the at least one piece of bolster material having a first bolster segment positioned to occur on a first side of the cutting path and a second bolster segment positioned to occur on a second side of the cutting path; and a retaining element adapted to hold the at least one piece of bolster material in association with the first arm working surface, the retaining element passing through the at least one piece of bolster material in at least one location in the first bolster segment and in at least one location in the second bolster segment, the retaining element presenting a plurality of loops longitudinally spaced from one another along a length of the at least one piece of bolster material and defining a receiving area arranged to receive the first arm of the surgical fastening apparatus, and the retaining element presenting a plurality of severable retaining element segments extending between the first and second bolster segments and positioned to occur in the cutting path upon application of the at least one piece of bolster material to the first arm working surface; wherein the plurality of severable retaining element segments are longitudinally spaced from one another along a length of the at least one piece of bolster material.

21. The medical device of claim 20, wherein the at least one piece of bolster material comprises a remodelable collagenous material.

* * * * *